US007858362B2

(12) United States Patent
Phillips et al.

(10) Patent No.: US 7,858,362 B2
(45) Date of Patent: Dec. 28, 2010

(54) METHOD OF USING ENDOPHYTIC FUNGI TO DECONTAMINATE AND DECOMPOSE HUMAN AND ANIMAL WASTES

(75) Inventors: Brian J. Phillips, Bozeman, MT (US); Gary Allan Strobel, Bozeman, MT (US); Emilie Dirkse, Madison, WI (US); David Ezra, Bozeman, MT (US); Uvidelio Castillo, Bozeman, MT (US)

(73) Assignees: Montana State Universtiy, Bozeman, MT (US); Phillips Environmental Products, Inc., Belgrade, MT (US)

( * ) Notice: Subject to any disclaimer, the term of this patent is extended or adjusted under 35 U.S.C. 154(b) by 455 days.

(21) Appl. No.: 11/569,181

(22) PCT Filed: May 25, 2005

(86) PCT No.: PCT/US2005/019240

§ 371 (c)(1), (2), (4) Date: Feb. 5, 2008

(87) PCT Pub. No.: WO2005/116272

PCT Pub. Date: Dec. 8, 2005

(65) Prior Publication Data

US 2009/0017526 A1 Jan. 15, 2009

Related U.S. Application Data

(60) Provisional application No. 60/574,895, filed on May 27, 2004.

(51) Int. Cl.
*C12S 3/00* (2006.01)
*C12S 3/24* (2006.01)
*C12N 1/14* (2006.01)
*A62D 3/02* (2007.01)

(52) U.S. Cl. ................. 435/267; 435/254.7; 435/254.1; 435/262.5; 435/264; 435/268

(58) Field of Classification Search ....................... None
See application file for complete search history.

(56) References Cited

U.S. PATENT DOCUMENTS

| | | | | |
|---|---|---|---|---|
| 3,895,116 | A | 7/1975 | Herting et al. | |
| 3,978,242 | A | 8/1976 | Freytag et al. | |
| 4,576,740 | A | 3/1986 | Hall et al. | |
| 4,954,497 | A | 9/1990 | Kamikado et al. | |
| 5,270,340 | A | 12/1993 | Kunisch et al. | |
| 5,612,338 | A | 3/1997 | Trah | |
| 5,968,964 | A | 10/1999 | Rehnig et al. | |
| 6,310,005 | B1 | 10/2001 | Assmann et al. | |
| 6,911,338 | B2 * | 6/2005 | Strobel et al. | 435/254.1 |
| 7,070,985 | B2 | 7/2006 | Strobel et al. | |
| 7,195,788 | B2 | 3/2007 | Roberts | |
| 7,267,975 | B2 | 9/2007 | Strobel et al. | |
| 7,341,862 | B2 | 3/2008 | Strobel et al. | |
| 2004/0018168 | A1 | 1/2004 | Strobel et al. | |
| 2004/0141955 | A1 | 7/2004 | Strobel et al. | |
| 2005/0220769 | A1 | 10/2005 | Strobel et al. | |
| 2006/0127346 | A1 | 6/2006 | Strobel et al. | |
| 2006/0127347 | A1 | 6/2006 | Strobel et al. | |

FOREIGN PATENT DOCUMENTS

| | | | |
|---|---|---|---|
| JP | 11-89562 | * | 4/1999 |
| JP | 11-089562 | A | 4/1999 |
| JP | 2001-233721 | * | 8/2001 |
| JP | 2001-233721 | A | 8/2001 |

OTHER PUBLICATIONS

Clement et al. "Stem-base disease and fungal colonization of winter wheat grown in compost inoculated with *Fusarium culmorum, F. graminearum* and Microdochium nivale". European Journal of Plant pathology. 1998, 104:323-330.*
Cilimburg et al. "Wildland Recreation and Human Waste: A review of Problems, Practices, and Concerns", Environmental Management, 2000, 25:587-598.
Strobel et al., "Bioprospecting for Microbial Endophytes and Their Natural Products", Microbiology and Molecular Biology Review, Dec. 2003, 67(4):491-502.
Nelson et al., "*Fusarium Species*: An Illustrated Manual for Identification", the Pennsylvania State University Press, 1983, Contents pages.
Strobel et al.,"Volatile Antimicrobials from a novel Endophytic Fungus", Microbiology, 2001, 147:2943-2950.
Szerszen et al., Effect of liquid manure on phytopathogenic soil fungi. *Polish Ecological Studies*, 1986, vol. 12, No. 1-2, pp. 123-128.
Pisarek et al., Effects of sewage sludge on the parameters of the crop production and influence on some phytogenic soil fungi. *Plant Protection Science*. 2002, vol. 38, Special Issue 2, pp. 692-695.
Strobel et al., "Volatile antimicrobials from *Muscodor albus*, a novel endophytic fungus", *Microbiology*, 2001, 147:2943-2950.
Worapong et al., "*Muscodor roseus* anam. Sp. nov., and endophyte from *Grevillea pteridifolia*", Abstract only, *Mycotaxon*, 2002, 81:463-475.
Sunesson et al., "Identification of Volatile Metabolites from Five Fungal Species Cultivated on Two Media", *Applied and Environmental Microbiology*, 1995, 61(8):2911-2918.

(Continued)

*Primary Examiner*—Vera Afremova
(74) *Attorney, Agent, or Firm*—Cooley LLP

(57) ABSTRACT

A method of treating human and/or animal waste products comprising contacting the waste products with an effective amount of *Fusarium culmorum* and *Muscodor albus*, together with a buffering agent and starch. The treatment process covered by the present invention can be employed in connection with pit toilets, portal a toilets, disposable waste bags, or any other environment in which the treatment of human and/or animal wastes is desired. Both the *Fusarium culmorum* and the *Muscodor albus* can be stored on infested seed grains, including, but not limited to, barley, rye, rice, wheat, mustard and grass. A method or preparing *Fusarium culmorum* for use in the treatment of human and/or animal wastes. An isolated culture of *Fusarium culmorum*. A composition comprising the same four elements used in the treatment process. A method for controlling the pH of a mixture of human liquid and sold wastes.

15 Claims, 5 Drawing Sheets

OTHER PUBLICATIONS

Nout et al., "Attraction of a Flying Nitidulid (*Carpophilius humeralis*) to Volatiles Produced by Yeast Grown on Sweet Corn and A Corn-based Medium", *Journal of Chemical Ecology*, 1998, 24(7):1217-1239.

Robinson et al., "Identification of Volatile Sporostatic Factors From Cultures of *Fusarium Oxysporum*", Trans. Br. Mycol. Soc. 1969, 52:293-299.

Landolt et al., "Trapping Social Wasps (*Hymenoptera : Vespidae*) with Acetic Acid and Saturated Short Chain Alcohols", *Journal of Economic Entomology*, 2000, 93(6):1613-1618.

Bartelt et al., "Volatiles from *Fusarium verticillioides* (*Sacc.*) Nirenb. And Their Attractiveness to Nitidulid Beetles," *Journal of Agricultural Food Chemistry*, 1999, 47(6):2447-2454.

Fiddaman et al. "The Production of Antifungal Volatiles by *Bacillus subtilis*", *Journal of Applied Bacteriology*, 1993, 74:119-126.

Filonow, "Mycoactive Acetate Esters from Apple Fruit Stimulate Adhesion and Germination of Conidia of the Gray Mold Fungus", *Journal of Agricultural Food Chemistry*, 2002, 50(11):3137-3142.

Filonow, "Germination and Adhesion of Fungal Conidia on Polycarbonate Membranes and on Apple Fruit Exposed to Mycoactive Acetate Esters", *Canadian Journal of Microbiology*, 2003, 49:130-138.

Humphris et al. "The Effects of Specific Volatile Organic Compounds Produced by *Trichoderma Spp.* on the Growth of Wood Decay Basidiomycetes", Abstract only, *Holzforschung*, 2001, 55:233-237.

McAfee et al., "A Review of the Volatile Metabolites of Fungi Found on Wood Substrates", *Natural Toxins*, 1999, 7:283-303.

Scholler et al., "Volatile Metabolites from Actinomycetes", *Journal of Agricultural Food Chemistry*, 2002, 50(9):2615-2621.

Tenuta et al., "Volatile Fatty Acids in Liquid Swine Manure Can Kill Microsclerotia of *Verticillium dahliae*", *Phytopathology*, 2002, 92(5):548-552.

Fischer et al., "Species-Specific Production of Microbial Volatile Organic Compounds (MVOC) by Airborne Fungi A Compost Facility", *Chemosphere*, 1999, 39(5):795-810.

Bacon et al., "Microbial Endophytes", Feb. 25, 2000, 1-21, Marcel Dekker, Inc., New York, NY.

Bjurman et al., "Volatile production by *Aspergillus versicolor* as a possible cause of odor in houses affected by fungi", *Mycopathologia*, 1992, 118:173-178.

Li et al., "Jesterone and hydroxy-jesterone antioomycete cyclohexenone eposides from the endophytic fungus *Pestalotiopsis jesteri*", *Phytochemistry*, 2001, 57:261-265.

Li et al., "Ambuic acid, a highly functionalized cyclohexenone with antifungal activity from *Pestalotiopsis spp.* and *Monochaetia sp.*" *Phytochemistry*, 2001, 56:463-468.

Li et al., "Cytocin, a potent tetramic acid antimycotoc from the endophytic fungus *Crytosporiopsis cf. quercina*", *Organic Letters*, 2000, 2:767-770.

Rapior et al., "The fenugreek oder of *Lactarius helvius*", *Mycologia*, 2000, 92:305-308.

Schnurer et al., "Fungal volatiles as sindicators of food and feeds spoilage", *Fungal Genetics and Biology*, 1999, 27:209-217.

Stierle et al., "Taxol and taxone production by *Taxomyces andreanae*, and endophytic fungus of Pacific yew", *Science*, 1993, 260:214-217.

Strobel et al., "OocydinA, a chlorinated macrocyclic lactone with potent anti-oomycete activity from *Serratia marcescens*", *Microbiology*, 1993, 145:3557-3564.

Worapong et al., "*Muscodor roseus* anam. gen. et sp. nov., An endophyte from *Cinnamomum Zeylanicum*", *Mytotaxon*, 2001, 79:67-79.

Rengpipat et al., "Characterization of a *Lactobacillus* Strain Producing White Crystals on Cheddar Cheese", *Applied and Environmental Microbiology* 1989, 55(10): 2579-2582.

O'Reilly et al., "Use of Hydrostatic Pressure for Inactivation of Microbial Contaminants in Cheese", *Applied and Environmnetal Microbiology* 2000, 66(11): 4890-4896.

* cited by examiner

SEQUENCE LISTING

```
<160> NUMBER OF SEQ ID NOS: 4

<210> SEQ ID NO 1
<211> LENGTH: 19
<212> TYPE: DNA
<213> ORGANISM: Artificial sequence
<220> FEATURE:
<221> NAME/KEY: primer_bind non-covalent
<222> LOCATION: 1..19
<223> OTHER INFORMATION: Universal primer ITS1

<400> SEQUENCE: 1
tccgtaggtg aacctgcgg                                              19

<210> SEQ ID NO 2
<211> LENGTH: 20
<212> TYPE: DNA
<213> ORGANISM: Artificial sequence
<220> FEATURE:
<221> NAME/KEY: primer_bind non-covalent
<222> LOCATION: 1..20
<223> OTHER INFORMATION: Universal primer ITS4
```

-continued

```
<400> SEQUENCE: 2
tcctccgctt attgatatgc                                               20

<210> SEQ ID NO 3
<211> LENGTH: 20
<212> TYPE: DNA
<213> ORGANISM: Artificial sequence
<220> FEATURE:
<221> NAME/KEY: primer_bind non-covalent
<222> LOCATION: 1..20
<223> OTHER INFORMATION: Universal primer SP6

<400> SEQUENCE: 3
catttaggtg aacactatag                                               20

<210> SEQ ID NO 4
<211> LENGTH: 19
<212> TYPE: DNA
<213> ORGANISM: Artificial sequence
<220> FEATURE:
<221> NAME/KEY: primer_bind non-covalent
<222> LOCATION: 1..19
<223> OTHER INFORMATION: Universal primer T7

<400> SEQUENCE: 4
gtaatacgac tcactatag                                                19
```

METHOD OF USING ENDOPHYTIC FUNGI TO DECONTAMINATE AND DECOMPOSE HUMAN AND ANIMAL WASTES

CROSS-REFERENCE TO RELATED APPLICATION

This application is a U.S. National Stage Entry and claims priority under 35 U.S.C. 371 of International Patent Application No. PCT/US2005/019240, filed on 25 May 2005, which claims priority to U.S. Provisional Application No. 60/574,895, filed on 27 May 2004. Both the International Application No. PCT/US2005/019240 and the U.S. Provisional Application No. 60/574,895 are hereby incorporated by reference in their entireties.

BACKGROUND OF THE INVENTION

1. Field of the Invention

The present invention relates to the discovery of non-pathogenic, endophytic fungi that, in combination with other agents, can decontaminate, degrade and deodorize human wastes. In the present invention, the appropriate combination of the harmless endophytic fungi *Muscodor albus* (*M. albus*) and a non-pathogenic strain of *Fusarium culmorum* (*F. culmorum*) and an appropriate buffer (mixed with starch) are placed together in any environment in which human or animal wastes are found. This combination of agents represents a safe and novel treatment process for the recycling of ingredients found in human and animal wastes. The presence of these two fungi effectively kills the harmful bacteria in the human wastes and at the same time begins the process of recycling the organic constituents of the wastes back to a harmless soil additive. The present invention also relates to the isolation and discovery of the particular endophytes that are the subject of this application and the necessary ingredients needed for them to effectively recycle the waste constituents.

2. Description of the Related Art

All publications and patent applications discussed herein are incorporated by reference to the same extent as if each individual publication or patent application were specifically and individually indicated to be incorporated by reference. The following description includes information that may be useful in understanding the present invention. It is not an admission that any of the information provided herein is prior art or relevant to the presently claimed inventions, or that any publication specifically or implicitly referenced is prior art.

This invention relates to the extremely important world problem of safely disposing of billions of pounds of human excrement each day. Only a fraction of this massive amount of material is safely treated, while the remainder is untreated and poses a threat to human health. For instance, it is well known that the complex of bacterial and other agents causing gastrointestinal diseases is the world's largest single cause of mortality. It is also well known that these types of diseases impact primarily infants and children. It is estimated that over the next ten years, at least twenty million people will die as a result of poor or inadequate sanitation facilities. Approximately half of the world's population (2.4 billion) is without adequate sanitation facilities. Nearly 6000 children die each day from conditions such as diarrhea. In addition, people suffering from water-borne diseases occupy about half of the world's hospital beds. In several Asiatic countries, twice as many people are dying from diarrhea-related diseases as from AIDS (1). Essentially, the poor sanitation conditions are resulting from or related to the inability of homes, communities and countries to adequately treat and dispose of human wastes, which bear and promote the growth and development of disease-causing microorganisms.

While this invention does not presuppose that all of the world's sanitation problems are to be solved with this treatment process, it does represent a solution to solving some sanitation problems that can be properly and safely handled. The treatment process of the present invention can be employed in connection with such activities as national emergencies, military maneuvers, marine-related activities, natural disasters, outdoor sporting activities (camping, hiking, canoeing, hunting, biking, etc.) and other activities in which human wastes need to be properly and safely disposed of. As an example, it has been recently noted that proper and safe disposal of human waste is an important concern for the appropriate management of wildland areas of the world. Aesthetics, as well as health concerns, are the major issues facing managers of these areas (2).

In the present invention, the endophytic fungi *M. albus* and *F. culmorum* are combined together in any environment where the degradation of human or animal wastes is desired. The wastes are then exposed to the volatile antibiotics of *M. albus* and the degradation capabilities of *F. culmorum*. While the use of *M. albus* to treat human and animal wastes is the subject of previously filed patent applications, the present application relates to the discovery that the degradation of human and animal wastes can be accelerated through the use of both *M. albus* and *F. culmorum* together and that the two fungi work synergistically to achieve this effect.

In an effort to identify another organism that could complement *M. albus* in this process, experiments were designed with the knowledge that *M. albus* normally either inhibits or kills most other fungi and bacteria. Specifically, experiments were designed to identify a microbe (fungus) that would not only tolerate the volatiles of *M. albus* but thrive on them and grow using human wastes as a food source. These experiments resulted in the discovery of *F. culmorum* and its effectiveness in treating human and animal wastes in conjunction with *M. albus*. In order to facilitate the survival of both *M. albus* and *F. culmorum* and their ability to grow on a mixture of liquid and solid human wastes, it was necessary to add a buffering agent and a readily available food source.

Accordingly, it is an object of the present invention to:

1. Identify an organism that will work together with and increase the efficacy of *M. albus* in safely treating human and animal wastes.

2. Identify an appropriate buffering agent for use in treating human and animal wastes with *M. albus* and *F. culmorum*.

3. Identify a suitable food source for the combination of *M. albus* and *F. culmorum* for use in the treatment of human and animal wastes.

BRIEF SUMMARY OF THE INVENTION

The present invention relates to the discovery that *M. albus* and *F. culmorum* can be used to effectively treat human solid and liquid wastes in any environment where the treatment of human and animal wastes is desired. These two unique fungi are compatible with each other, and each performs a useful function in the biodegradation of the wastes. *M. albus* effectively carries out bacterial decontamination, while the *F. culmorum* biodegrades the wastes. The growth of each fungus must be optimized to achieve the optimal effect. This is accomplished by controlling the pH of the solid and liquid wastes as they get mixed during the waste relief activities. In addition, the fungi execute their respective functions more effectively if they are given an easily digestible carbon source to initiate growth. To address both the buffering and the food source needs, the present invention includes a mixture of buffering agent and starch that is added to the combination of fungi and wastes in an amount appropriate to control pH and initiate fungal growth. These new developments will allow for the safe and rapid decontamination of human wastes and provide for the rapid reintroduction of organic materials back to the environment from which they came.

DETAILED DESCRIPTION OF THE INVENTION

Figure 1:
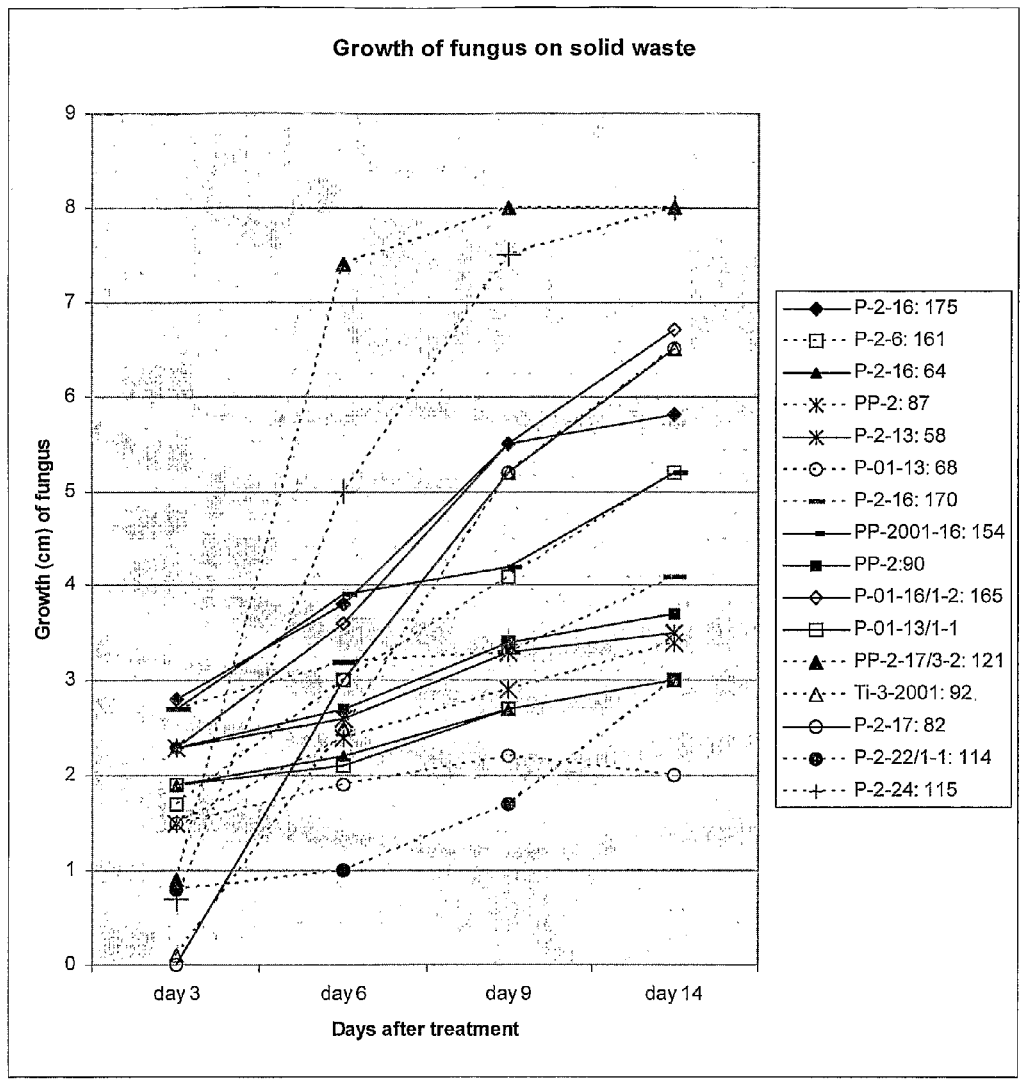
FIG. 1 is a graph representing the growth of sixteen different endophytic fungi on about one gram of solid human waste over a fourteen-day period.

Microorganisms living in the world's rainforests, in order to survive, must have evolved biochemical mechanisms to cope with potential competitors. In this regard, they developed an ability to produce molecules that are antimicrobial and compounds that inhibit and destroy other microbes. Because new antibiotics are sought after by mankind, researchers visit rainforests in search of new microbes and the agents that they produce to inhibit and destroy other microbial competitors. *M. albus*, which decontaminates human wastes, was discovered in the rainforests of Honduras.

Decontaminating human wastes is only one problem associated with the waste treatment process. An additional problem that needs to be addressed is the need to begin the immediate degradation process of the organic material in the solid and liquid wastes. *M. albus*, by itself, will not fully degrade all of the organic constituents found in human wastes. In order to find an organism that would work with *M. albus* to accomplish this result, it was assumed that microbes living within plants (namely, the endophytes) would be an appropriate place to begin the search.

Endophytes are the first microbes that are involved in the degradation of a plant when it dies of either natural causes or environmental damage. They have a set of enzymes that degrades the cellulose, lignin and hemicelluloses found in plant materials. These are the same complex organic materials that are found in human solid wastes; therefore, in order to tackle the problem with which the present application is concerned, namely, the degradation of human and animal wastes, a number of endophytic microbes were located and tested for their ability to grow on both solid and liquid human wastes. In order for the microbe to work in concert with *M. albus*, however, it must be insensitive to the volatile antibiotics produced by *M. albus*. For that reason, the research process focused on identifying endophytic microbes that not only flourish on human wastes but also that are not inhibited by the *M. albus* volatiles.

To facilitate the growth of these organisms, it was necessary to ascertain whether any factors present in the combination of liquid and solid wastes might preclude fungal development. In this regard, it was discovered that within minutes of mixing solid and liquid wastes, the pH of the mixture begins to increase. After 48 hours, the pH reached 10.0+, which is well beyond the range for optimal growth of *M. albus* and *F. culmorum*. This problem was solved by adding crystalline phosphoric acid and a starch ingredient to the mixture of wastes and fungi. Other acids that could function in the same manner as phosphoric acid within the context of the present invention are citric acid, malonic acid, succinic acid, maleic acid, glutaric acid, tartaric acid, and any other naturally occurring acid that will provide the necessary buffering capacity for the growth of the fungi.

Discussed below are the various experiments that resulted in the discovery of *F. culmorum* and the phosphoric acid/starch system for use in combination with *M. albus* in treating human and animal wastes. The combination of *F. culmorum*, *M. albus* and the phosphoric acid/starch system discussed herein can be used to decontaminate, degrade and deodorize human and animal wastes not in any environment in which there is a presence of human and/or animal wastes, including, but not limited to, pit toilets, portable toilets, feed lots, sewage holding areas, and any container or containment area where there is an accumulation of human and/or animal waste.

A strain of *F. culmorum* was deposited with the Centraalbureau voor Schimmelcultures in the Netherlands on 19 Feb. 2004 and has been assigned deposit number CBS 114573. Although the P-2-24:115 strain of *F. culmorum* is described in the experiments below, the present invention encompasses all strains of *F. culmorum*, as well as any derivative, recombinant, or variant thereof that performs the function described herein. A strain of *M. albus* was deposited with the Agricultural Research Service Culture Collection (NRRL) on 1 Feb. 2002 under Accession No. 30547 in connection with U.S. patent application Ser. No. 10/121,740.

1. EXAMPLE 1

Initial Screening for Endophytic Fungi Growing in the Presence of *M. albus*

The purpose of this experiment was to find a non-pathogenic, endophytic fungus that will decompose waste in the biodegradable WAG BAG® in the presence of *M. albus*. The WAG BAG® is a commercially available product of Phillips Environmental Products, Inc. ("Phillips Environmental Products"). The WAG BAG® is a disposal kit for human waste that contains a blend of a super-absorbent polymer (preferably, sodium polyacrylate), a deodorizer (preferably, zeolite), and a decay catalyst (preferably, catalytic yeast enzymes) in a 1.5 mil thick waste collection bag, which in turn is packaged in a 2 mil thick outer bag. The absorbent stabilizes the contents of the WAG BAG® for safe transportability, and the deodorizer provides instant odor reduction. The WAG BAG® also includes a 3 mil thick disposal bag, towelette, and toilet paper. All three bags that make up the WAG BAG® are made out of a biodegradable linear low-density polyethylene.

For this purpose, hundreds of endophytic fungi obtained from plants growing in the Amazonian rainforests of Peru were obtained by standard methods of isolation (3). These organisms were then subjected to the gases of *M. albus* to determine their sensitivity to it. Those organisms that were insensitive to the *M. albus* gases were then tested for their ability to grow on both solid and liquid human wastes.

Divided Petri dishes with four compartments served as the basis of the bioassay system. *M. albus* was grown in one compartment on potato dextrose agar (PDA), and the three other compartments were supplied with a small agar block supporting test microbes from Peru. Plates were checked daily, and test fungi showing viability after a three-day exposure were set aside and utilized in the following experiment. Over twenty fungi were able to grow in the presence of *M. albus*. These fungi were then systematically tested for their ability to grow on solid human wastes and 16 of these were more carefully examined for their growth characteristics on human wastes.

2. EXAMPLE 2

Fungal Growth on Solid Waste

Test fungi demonstrating the ability to grow in the presence of *M. albus* were grown on PDA for seven days in order to develop an inoculum base for testing on solid human waste. For each test fungus, 1 g of fresh solid waste from a healthy 22-year-old female was placed in the center of a Petri plate. A test fungus was obtained by cutting the mycelium on the agar cut into small cubes ($\frac{1}{2} \times \frac{1}{2} \times \frac{1}{2}$ cm$^3$) using sterile techniques and then placing it on top of the solid human waste dollop (about 1 gram). Data were collected over a 14-day period regarding the diameter growth of each test fungus, the degree of bacteria growth, and the attractiveness of the fungus toward the waste dollop (see Example 3 below for an explanation of how "attractiveness" was measured). As shown in FIG. 1, each of the fungi tested showed growth on the dollop of human waste; however, the fungi P-2-16:64 and P-2-24:115 showed the best mycelial growth. The other fungi clustered at the lower half of the graph, indicating a much lower rate of growth.

3. EXAMPLE 3

Ability to Inhibit Bacterial Growth

Because bacteria are the main microbial and most harmful constituents of human solid wastes, 16 of the 20 endophytic fungi were then tested for their ability to inhibit bacterial growth. The degree of bacterial growth was measured visually by:–(lots of bacterial growth), +–(some bacterial growth), +(slight bacterial growth), and ++(no bacterial growth). In addition, the degree of attractiveness of the individual fungus towards the dollop was measured visually by: –(growth away from dollop), +–(slight growth towards dollop), +(attachment to dollop), ++(growth covering dollop). Data were assessed after 14 days. As shown in Table 1 below, in many cases bacterial growth was rampant in the presence of the endophytic fungus (see, for example, P-2-16:175); however, the fungus P-01-13/1-1:32 precluded all observable bacterial growth. The fungi having a single +(inhibition of most bacterial growth) were represented by such fungi as P-2002-16:154 and P-2-24:115.

4. EXAMPLE 4

Ability to Grow and Cover the Dollop and Degree of Attractiveness to the Dollop Referring to Table 1, several fungi met the criteria for being attracted to the dollop of human wastes. Many of the other fungi either grew away from the dollop or were only weakly attracted to it. Data were assessed after 14 days.

TABLE 1

| Fungus | Bacterial growth | Attractiveness |
|---|---|---|
| P-2-16: 175 | – | – |
| P-2-6: 161 | +– | – |
| P-2-16: 64 | – | – |
| PP-2: 87 | + | +– |
| P-2-13: 58 | – | – |
| P-01-13: 68 | – | – |
| P-2-16: 170 | – | +– |
| PP-2001-16: 154 | + | + |
| PP-2: 30 | – | +– |
| P-01-16/1-2: 165 | + | + |
| P-01-13/1-1: 32 | ++ | ++ |
| PP-2-17/3-2: 121 | +– | +– |
| Ti-3-2001: 92 | +– | ++ |
| P-2-17: 82 | +– | + |
| P-2-22/1-1: 114 | + | ++ |
| P-2-24: 115 | + | ++ |

5. EXAMPLE 5

Fungal Growth on a Dollop with No Starting Food Base

Figure 2:
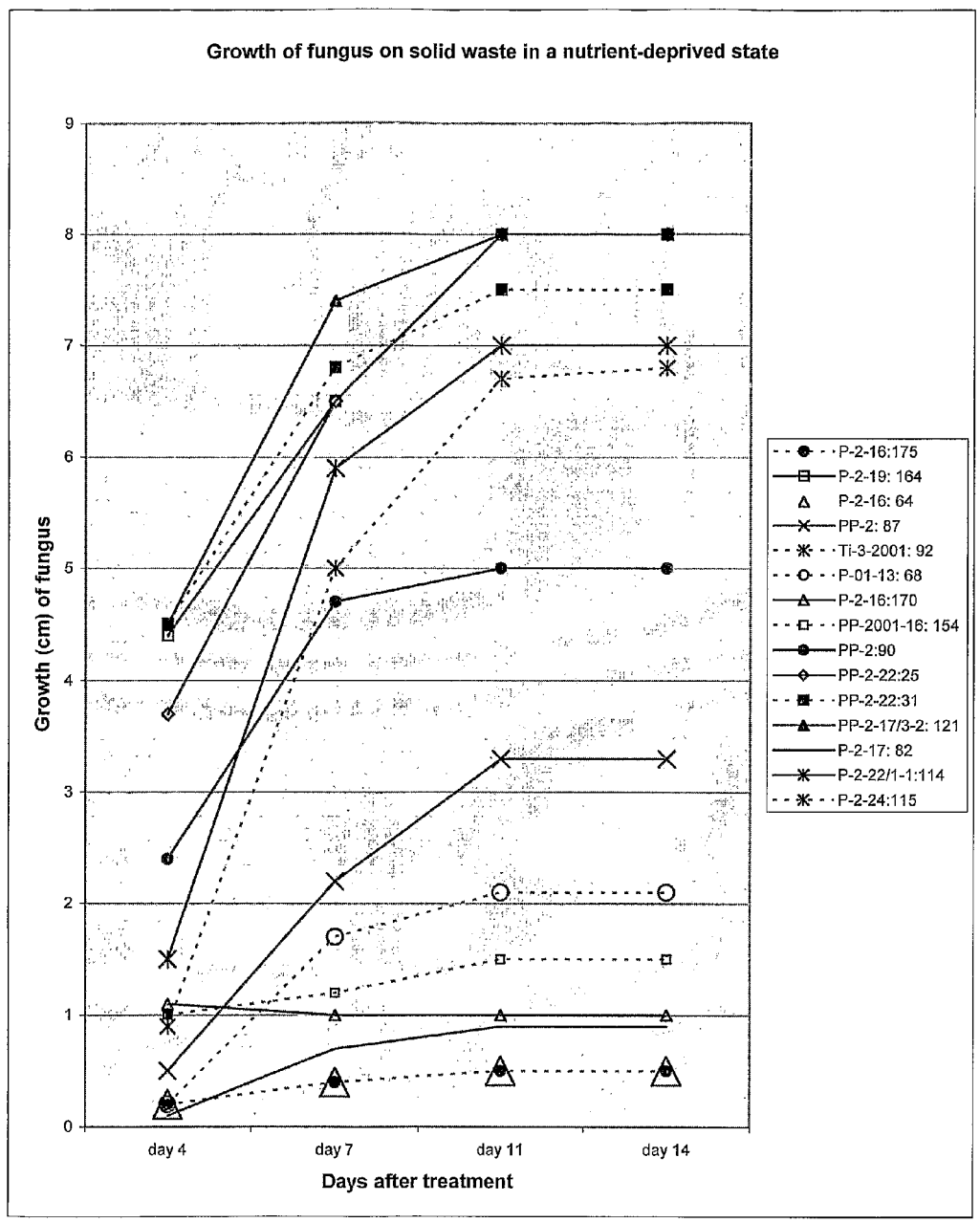
FIG. 2 is a graph representing the growth of test fungi grown in a nutrient-deprived state on solid waste.

This experiment was conducted to determine whether the nutrients in the PDA agar base were supporting the growth of the fungus rather than the ingredients of the waste dollop. The fungi were inoculated on the dollop having been grown on only water agar that contains absolutely minimal nutrients. For each test fungus, a plate was equipped with water agar medium supporting the test fungus and a one-gram dollop of solid waste. The water agar was utilized in order to illustrate a nutrient-deprived state of the fungus. Each test fungus was grown on water agar for seven days. Using sterile technique, small cubes (as described earlier) were cut from fungal plates and positioned on top of the waste dollop. Observations pertaining to the growth over 14 days were recorded. As shown in FIG. 2, fungi P-2-24:115 and P-2-17:32 demonstrated the best growth on the dollop after two weeks, with the majority of other fungi showing a much weaker response after two weeks.

6. EXAMPLE 6

Fungal Growth in Liquid Waste

Figure 3:
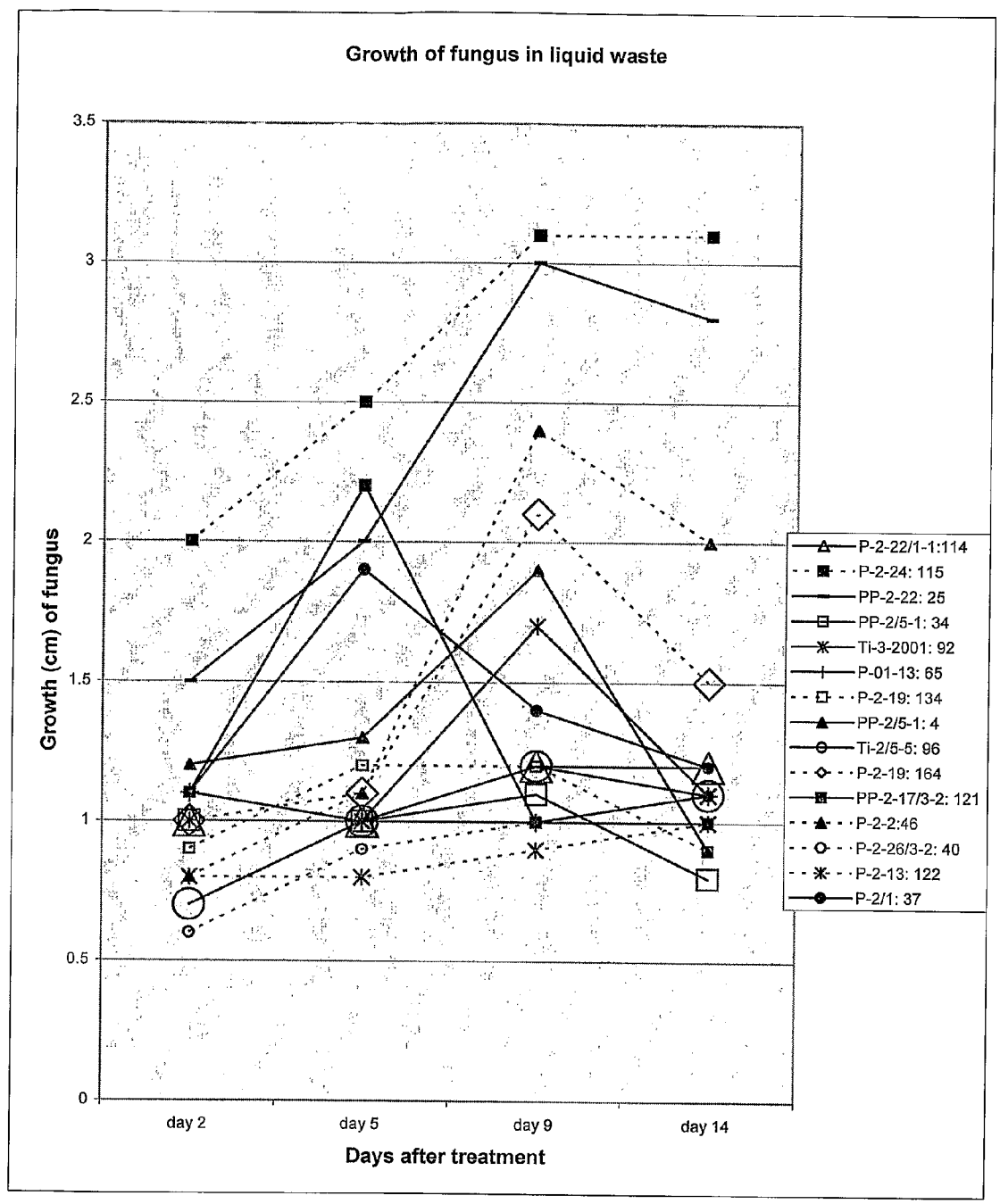
FIG. 3 is a graph representing the growth of test fungi grown in urine over a fourteen-day period.

Test endophytic fungi demonstrating the ability to grow rapidly and also having shown the prevention/inhibition of bacterial growth (Table 1) were grown on PDA for seven days. Fungi were removed from the agar plate by cutting a $\frac{1}{2} \times \frac{1}{2}$ cm$^2$ piece and placing it in 8 ml of fresh (<1 hr) urine. Data were recorded and observed over a 14-day period. As shown in FIG. 3, the fungus demonstrating the best growth by far was P-2-24:115.

7. EXAMPLE 7

Fungal Growth in Liquid and Solid Wastes

Figure 4:
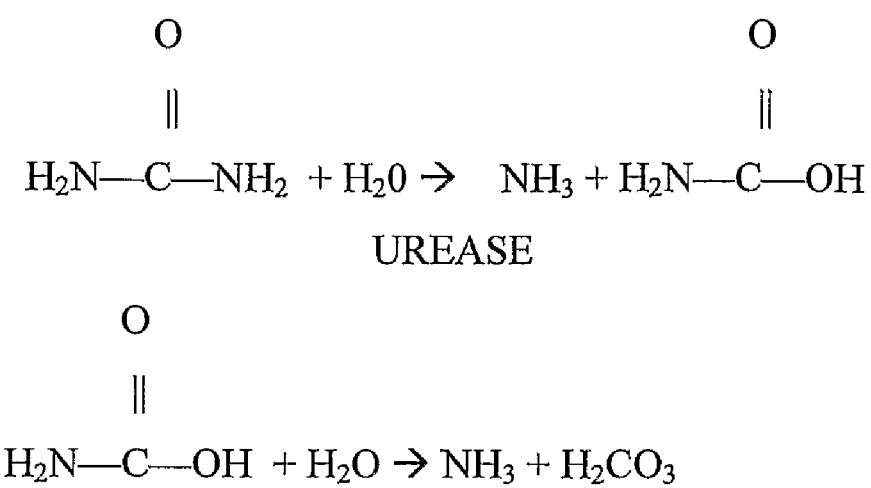
FIG. 4 is a diagram illustrating the hydrolysis of urea to ammonia and carbamate with assistance from the enzyme urease. This diagram also illustrates the spontaneous hydrolysis of carbamate to carbonic acid and a second molecule of ammonia.
Figure 5:
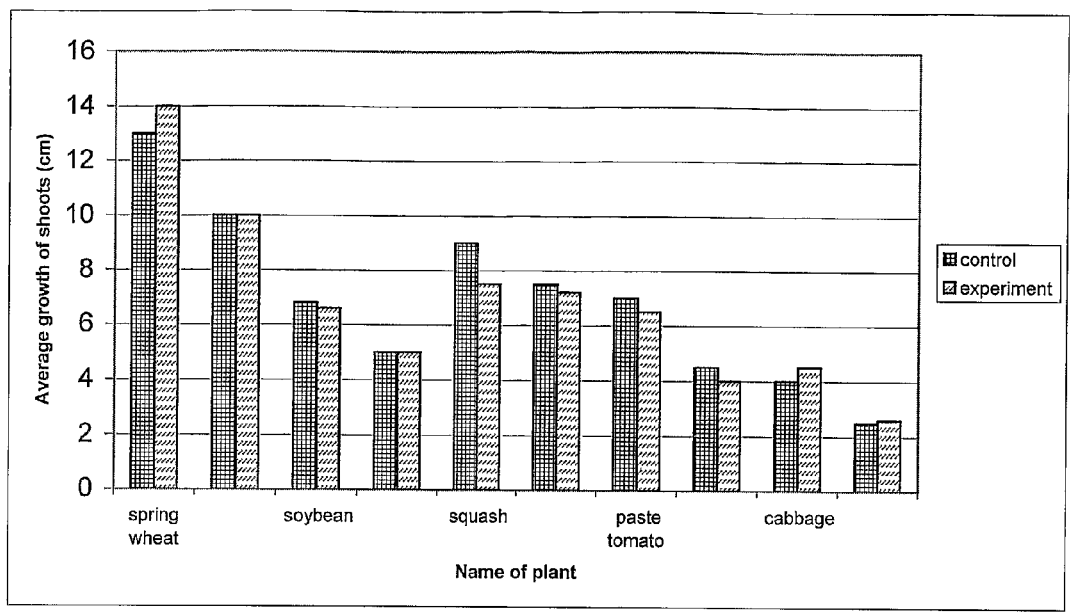
FIG. 5 is a graph representing the average growth of various types of shoots after six weeks.

Because humans are unique in normally depositing both liquid and solid wastes at the same location and at the same time, this factor was taken into consideration in developing a method of biological treatment. As shown in FIGS. 1 and 3, test fungi indicative of rapid growth on solid and in liquid waste were grown on PDA for 7 days. For each fungus, 6 ml of urine and 1 g of solid waste were added to a sterile Petri dish. Using sterile technique, a ½×½ cm² agar block (PDA) supporting the mycelium of the given test fungus was emerged into the waste mixture. For most test fungi, growth halted after 24 hours, and further examination after 24 hours showed no improvement of growth. Because test fungi grew on solid waste and in liquid waste separately (see FIGS. 1 and 3), it was concluded that an enzymatic reaction was causing the inhibition of growth. The pH of the mixture (liquid and solid wastes) rose initially from neutral (pH 6-7) to basic (pH 11) within 48 hours. The enzymatic reaction produces excess ammonia, thus causing the pH to rise (FIG. 4). Due to the fact that most fungi do not grow in an extremely basic environment, it was determined that either a buffer or urease inhibitor be added to allow growth. The function of the urease enzyme is shown in FIG. 4. Ureases are found in a wide assortment of different organisms, many have been isolated from various bacteria, fungi and higher plants. None of the urease inhibitors was satisfactory, and tests were then established using different buffers and buffer concentrations.

8. EXAMPLE 8

Selection of an Appropriate Fungus for Waste Degradation

Of all of the endophytic fungi that were tested for their growth on liquid and solid wastes, their relative ability of inhibit bacterial growth, and their ability to thoroughly cover the dollop of solid waste, the fungus that outperformed the others was isolate P-2-24: 115 (FIGS. 1, 2 and 3 and Table 1). This organism had been isolated form the cloud forest plant *Dunalia purpurea*. Despite this finding, it was still necessary to solve the problem associated with the appearance of no growth of any fungus on a mixture of both liquid and solid wastes. To address that problem, an experiment was conducted to test various buffers.

9. EXAMPLE 9

Fungal Growth in the Presence of a Buffer

Due to the high pH caused by ammonia formation, there was a need for an efficient, inexpensive powder/solution with a high buffering capacity. Silica, charcoal, starch, trehalose, glycine, potassium phosphate, sulfate, citrate, and phosphoric acid were assessed. Silica in the presence of glycine did not show any buffering capabilities. After numerous experiments, phosphoric acid was selected as the optimal buffer because of the fact that it has three pKa's, each of which acts as a buffer. The combination of starch and phosphoric acid exhibited the best results. Starch accelerated the initial growth of the fungi, and small amounts of phosphoric acid prevented the waste mixture from continuously increasing in pH. Crystalline phosphoric acid in the presence of pure potato starch at a ratio of at least 1:10 was the best additive to facilitate the growth of both M albus and the fungus P-2-24: 115 on the mixture of solid and liquid human wastes under the conditions described in Example 7. Other starches that could be used in lieu of potato starch are corn starch, rice starch, cassava starch and any other starch from a plant source that is finely ground and capable of being mixed with the buffering agent.

10. EXAMPLE 10

Fungal Growth in Polymer

All tests were replicated using 125 mg of sodium polyacrylate from the WAG BAG®, 1 g of solid waste, and 6 ml of urine and the phosphoric acid/starch combination. The purpose of the experiment was to determine whether the sodium polyacrylate had an effect on the growth of test fungus. After data analysis, it was verified that the sodium polyacrylate had no inhibiting effects on the growth rate of test fungi. The sodium polyacrylate is used to facilitate the immobilization of liquid wastes in the WAG BAG®.

11. EXAMPLE 11

Storage of the Fungus

The selected fungus was isolated from a Solanaceous plant, *Dunalia purperea*, in Peru. Agar plugs containing the fungus were placed in 15% glycerol and stored at −70° C. *M. albus* is also stored in this manner or on infected barley seeds at 4° C., room temperature or −70° C. The *F. culmorum* can be stored on barley seeds, or any other seed grain, in the same manner as *M. albus*. The method of storing *M. albus* on seed grain was previously described in U.S. application Ser. No. 10/408,209, filed on Apr. 4, 2003, and U.S. application Ser. No. 10/802, 975, filed on Mar. 17, 2004, which are incorporated herein by reference.

12. EXAMPLE 12

Identification of the Endophytic Fungal Isolate P-2-24:115

It was essential that if isolate P-2-24:115 were to be used in the treatment of human wastes, it had to be taxonomically identified. On PDA, growth is rapid, with dense aerial mycelium and a carmine red undersurface. Microconidia from aerial mycelium were scarce to none, and chlamydospores were present. Macroconidia from sporodochia were stout with thick walls, and the shape of the basal and apical cells were nipple-like, sometimes strongly curved as a beak. The color of the aerial mycelium is tan and brown, and the color of the colony is carmine red. The spore masses are orange concentrated in the center of the colony. Based on morphology, P-2-24 was identified as *Fusarium culmorum* (4). Organisms of this type appear to be relatively stable in culture, but mutants may occur. In addition, *F. culmorum* is reported to be toxigenic (4). This organism was further characterized via molecular biology techniques.

13. EXAMPLE 13

Fungal DNA Isolation

P-2-24 was grown in 100 ml of PDB (potato dextrose broth) for seven days at 23° C. The mycelia were harvested by filtration through cheesecloth. Total genomic DNA was extracted by Qiagen DNeasy Plant Mini Kit (Qiagen, Inc.). Aliquots (20 μl) of total genomic DNA were electrophoresed through agarose gels (1.5% w/v), prepared using TAE buffer (40 mM Tris base, 1 mM EDTA, 20 mM acetic acid), stained with ethidium bromide, viewed under UV light and photographed.

14. EXAMPLE 14

PCR Amplification of Internal Transcribed Space Sequences (ITS) and 5.8s rDNA ITS 1 and 2 regions of P-2-24 were amplified using PCR and the universal ITS primers ITS1 (5' TCCGTAGGTGAAC-CTGCGG 3' [SEQ ID NO. 0001]) and ITS4 (5' TCCTC-CGCTTATTGATATGC 3' [SEQ ID NO. 0002]) (see Table 2). The polymerase chain reaction (PCR) was performed in a 25 μl reaction containing 10 mM of each primer, 0.1 μg of total genomic DNA, 3 mM of the 4 dNTPs, and 0.5 U of Nova Taq DNA polymerase in a 10× Nova Taq Buffer with MgCl$_2$ (10×=100 mM Tris-HCl pH 9.0 at 25° C., 500 mM KCl, 15 mM MgCl$_2$ 1% Triton X-100). The following cycle parameters were maintained: 95° C. for five minutes followed by 34 cycles of 40 seconds at 95° C., 40 seconds at 45° C. and 40 seconds at 72° C. followed by five minutes at 72° C. The PCR products were purified using the QIAquick PCR Purification Kit (Qiagen). Amplification was performed in a Biometra T Gradient DNA thermal cycler. Aliquots (2 µl) of amplification products were electrophoresed through agarose gels (1.5% w/v).

15. EXAMPLE 15

DNA Cloning

The PCR product was cloned into a pGEM Easy T vector (Promega) according to manufacturer's instructions.

16. EXAMPLE 16

Transformation and Extraction

Preparation of competent cells was performed by the CCNB80 method. *E. coli* (DH5a) was grown to 0.3 OD at 595 nm (LB, 100 rpm, 37° C.). The culture was chilled on ice for ten minutes. The cells were then pelleted by centrifugation for ten minutes at 4° C. at 5000 rpm. The pellet was resuspended in ⅓ of the original volume of cold CCNB80 (for 1 L-10 ml KAct, 2 g MgCl$_2$, 4 g MnCl$_2$, 11.8 g CaCl$_2$, 100 ml glycerol). This suspension was left on ice for 20 minutes, repelleted, and resuspended in CCNB80 (¹⁄₁₂ the original volume). This suspension was incubated on ice for ten minutes and then divided into 200 µl aliquot in Eppendorf vials and immediately frozen in −80° C. The DNA transformation into the cells was performed according to standard procedures (5). The transformed cells were plated on LB agar supplemented with 30 µg/ml ampicillin (Sigma), in the presence of IPTG and X-gal for blue/white selection. White single colonies were grown in LB broth, and DNA was extracted using Perfectprep Plasmid Mini (Eppendorf) according to manufacturer's instructions. Presence of the insert was confirmed by direct colony PCR with SP6 (5'CATTTAGGTGAACACTATAG 3' [SEQ ID NO. 0003]) and T7 (5'GTAATACGACTCACTATAG 3' [SEQ ID NO. 0004]) universal primers and by DNA digestion with EcoRI restriction enzyme (Promega).

17. EXAMPLE 17

Cycle Sequencing ITS Regions and 5.8S rDNA

The plasmid inserts were sequenced by the Plant-Microbe Genomics Facility at Ohio State University using an Applied Biosystems 3700 DNA Analyzer and BIGDYE Terminator Cycle Sequencing chemistry and the universal primers SP6 and T7.

TABLE 2

| Primers | Sequences from 5' to 3' | SEQ ID NO. |
|---|---|---|
| ITS1 | 5' TCC GTA GGT GAA CCT GCG G 3' | 0001 |
| ITS4 | 5' TCC TCC GCT TAT TGA TAT GC 3' | 0002 |

TABLE 2-continued

| Primers | Sequences from 5' to 3' | SEQ ID NO. |
|---|---|---|
| SP6 | 5' CAT TTA GGT GAA CAC TAT AG 3' | 0003 |
| T7 | 5' GTA ATA CGA CTC ACT ATA G 3' | 0004 |

18. EXAMPLE 18

Sequence Analysis

Comparison and alignment sequences were done by using standard nucleotide-nucleotide BLAST [blastn] in the NCBI at the web site (http://www.ncbi.nlm.nih.gov/BLAST) and by manually aligning them afterwards. The ITS1-2 sequences of culture collection P-2-24 were submitted to the GenBank database under accession number AY260958.

19. EXAMPLE 19

Molecular Biology of P-2-24

The partial sequences of ITS1, 5.8S, and ITS2 have been demonstrated to be highly conserved regions of DNA and therefore very useful in the classification of organisms. These molecularly distinguishing partial sequences of *F. culmorum* were obtained and compared to the data in GenBank. Comparative analysis of the partial ITS 1&2 and 5.8S rDNA sequences of P-2-24 hit 99% matches with *F. culmorum* isolate FC32 (AY147318), *F. culmorum* isolate FC12 (AY147315), *F. culmorum* isolate ITCC146 (AY147305), *F. culmorum* isolate CSF2 (AY147296), and *F. culmorum* isolate CAF5 (AY147290). Based on these matches and the morphological features indicated above, the isolate P-2-24: 115 is identified as *Fusarium culmorum*. It has been deposited in the MONT herbarium as a living specimen as P-2-24-*Fusarium culmorum*.

20. EXAMPLE 20

Comparison of P-2-24 with other *Fusarium* spp

The question arose whether other *Fusarium* species, both standards and endophytes, share the characteristic ability to grow and decompose waste materials. An experiment was conducted with liquid and solid wastes, buffer, starch, and a number of controls, P-2-24, 169, 1631, 1697 (these are all *Fusarium* endophytes found in the tropics), along with standard *F. culmorum*, *F. avenaceum*, *F. solani*, and *F. oxysporum* available in the USA. The table below reveals the amounts of additives used in the experiment. Starch is supplemented to initially accelerate growth, and phosphoric acid is used as a buffer as described above. The terms "liquid" and "solid" refer to freshly acquired urine and feces, respectively. Endophytic *Fusarium culmorum* P-2-24: 115 produced the best growth, along with the standard plant pathogenic *F. culmorum*.

TABLE 3

| Name/# of fungus | | starch | acid | polymer | liquid | solid | pH | growth |
|---|---|---|---|---|---|---|---|---|
| P-2-24 | Endophyte | 500 mg | 30 µl | 125 mg | 6 ml | 1 g | 7.0 | 8.0 cm |
| 169 | Endophyte | 500 mg | 30 µl | 125 mg | 6 ml | 1 g | 7.0 | 0.0 cm |
| 1631 | Endophyte | 500 mg | 30 µl | 125 mg | 6 ml | 1 g | 6.5 | 0.6 cm |
| 1697 | Endophyte | 500 mg | 30 µl | 125 mg | 6 ml | 1 g | 7.0 | 4.5 cm |
| F. culmorum | Standard | 500 mg | 30 µl | 125 mg | 6 ml | 1 g | 8.0 | 8.0 cm |
| F. avenaceum | Standard | 500 mg | 30 µl | 125 mg | 6 ml | 1 g | 8.0 | 5.4 cm |
| F. solani | Standard | 500 mg | 30 µl | 125 mg | 6 ml | 1 g | 7.0 | 2.5 cm |
| F. oxysporum | Standard | 500 mg | 30 µl | 125 mg | 6 ml | 1 g | 7.0 | 1.8 cm |

Thus, although the standard *F. culmorum* isolate compared favorably in its growth characteristics to the *F. culmorum* isolate P-2-24:115, it could not and would not be incorporated into the WAG BAG® because of its inherent plant pathogenicity.

21. EXAMPLE 21

Preliminary Greenhouse Experiments

The members of the genus *Fusarium* are among the most important plant pathogens in the world; therefore, we wished to determine if *F. culmorum* isolate P-2-24 was pathogenic to the normal range of plants, as is the standard pathogenic isolate of *F. culmorum*. Based on the availability of seeds, a number of host plants subject to disease caused by *Fusarium* were selected. The following plants were tested: spring wheat, tall fescue, butterbaby soybean, evergreen hardy green onions, butternut squash, Mary Washington asparagus, ropreco paste tomato, 4$^{th}$ of July tomato, golden acre cabbage, and carnation. Seeds were grown for six weeks in metal potting trays (12"×14"). Soil for treatments and controls were not sterilized because the intent was to reproduce natural settings. *Fusarium culmorum* P-2-24 was inoculated and grown on sterile barely seeds for two weeks. Seeds of the selected plants were sown in rows according to directions, and 3-4 (~28 mg) inoculated barely seeds were placed in between sown seeds (see Table 4). For each treatment, a control without any inoculum was used. Plants were fertilized once weekly at 200 ppm (standard mix), grown for six weeks, and then evaluated. Roots and shoots were harvested and visually evaluated by measuring the height of the shoot, the percentage of root system coverage with lesions, and the overall physical appearance.

TABLE 4

| Plant | Planting depth | # of seeds/pod | # of pods/row |
|---|---|---|---|
| Spring Wheat | 1-2" | 4-5 seeds | 6 pods/row |
| Tall Fescue | 2" | 4-5 seeds | 4 pods/row |
| Soybean | 2-3" | 2-3 beans | 4 pods/row |
| Green onions | ¼-½" | 1-3 seeds | 6 pods/row |
| Squash | ¾-1" | 4-6 seeds | 4 pods/row |
| Asparagus | ½" | 2-3 seeds | 4 pods/row |
| Tomato | ¼-½" | 1-2 seeds | 4 pods/row |
| 4$^{th}$ of July tomato | ¼" | 1-2 seeds | 4 pods/row |
| Cabbage | ¼" | 3-4 seeds | 4 pods/row |
| Carnation | ¼" | 1 seed | 3 pods/row |

TABLE 5

| Plant | Visual root damage (%) | Physical appearance |
|---|---|---|
| Spring Wheat | 0% | Healthy-looking |
| Tall Fescue | 0% | Healthy-looking |
| Soybean | 0% | Healthy-looking |

TABLE 5-continued

| Plant | Visual root damage (%) | Physical appearance |
|---|---|---|
| Green onions | 0% | Healthy-looking |
| Squash | 0% | Healthy-looking |
| Asparagus | 0% | Healthy-looking |
| Tomato | 0% | Healthy-looking |
| 4$^{th}$ of July tomato | 0% | Healthy-looking |
| Cabbage | 0% | Healthy-looking |
| Carnation | 0% | Healthy-looking |

No external symptoms of disease were visually observed on any of the plants, and the inoculated plants grew as well as the controls (see FIG. 5; see also Tables 4 and 5). There are a number of different factors that could have prevented accurate visual diagnoses; plants could have been watered too much, thus preventing the fungus from attacking the root system, the stem base disease symptoms could be difficult to assess visually, or the length of the time for growth could have been too short. Based on these results and the fact that the original host plant from which the *F. culmorum* was isolated was symptomless, it was concluded that the organism is non-pathogenic.

22. EXAMPLE 22

Testing of *F. culmorum* and *M. albus* in the WAG BAG® Complete with all Constituents A test was devised in which the WAG BAG® (with the contents noted above under Example 1), including a full complement of both liquid and solid human wastes, was buried in soil at 22° C. for periods of three to six weeks and then assessed for odor, fungal growth, decay as measured visually, and bacterial decontamination. In this experiment, the *M. albus* and starch and phosphoric acid were placed directly on top of the wastes in the WAG BAG®. The components of each bag contained the following complete complement of ingredients: starch/phosphoric acid (16/1 W/W) –3.25 g; *M. albus* grown on autoclaved barley seed—7.5 g; *F. culmorum* having been grown on autoclaved barley seed 3.25 g; and sodium polyacrylate at 10 g. For testing purposes the ingredients of the bags were modified in order to study the effects of each ingredient on the waste treatment processes (see Table 6). Odor, fungal growth and waste decay were measured visually and rated according to a ranking system as shown in Table 6.

Bacterial contamination was measured by sampling 1 mg of waste, diluting it in a serial manner on nutrient agar plates, and subsequently counting the number of bacterial colonies after 48 hours.

TABLE 6

| Treatment | Bacterial colonies | Odor | Decay | Fungal Growth |
|---|---|---|---|---|
| M + F + SP + SPA | $3.5 \times 10^5$ | 2* | 3* | 4* |
| F + SP + SPA | $4.0 \times 10^8$ | 3* | 3* | 3* |
| M + SP + SPA | $1 \times 10^6$ | 3* | 3* | 3* |
| M + SP + SPA(top) § | 0 | 3* | 3* | 3* |
| SPA(control) | $1.75 \times 10^8$ | 5* | 1* | 1* |

Legend: M = *M. albus*; F = *F. culmorum*; SP = starch-phosphoric acid; SPA = sodium polyacrylate.
Each component was added at the level as indicated above.
Odor: 1* = no odor ranging to 5* = absolutely untolerable
Decay: 1* = no decay ranging to 5* = completely decayed
Fungal Growth; 1* = no growth ranging to 5* = completely covering the wastes.
§ indicates placement at the top of the wastes in the WAG BAG ®.

It was observed that *F. culmorum* by itself did not reduce the bacterial population of the wastes and had little effect on the odor reduction. By the same token, *M. albus* reduced bacterial contamination, reduced odor, and did produce abundant fungal growth on the wastes. Furthermore, if the *M. albus* and S&P [starch and phosphoric acid] were added to the top of the wastes in the WAG BAG®, there were no recoverable bacteria in the WAG BAG® after six weeks. A treatment (control) with only the SPA [sodium polyacrylate] had no effect on any of the parameters being measured.

Ultimately, both fungi (*M. albus* and *F. culmorum*), the starch/phosphoric acid mixture, and the SPA dramatically reduced bacterial numbers, improved the decay of the wastes, reduced odors and produced a mycelium that almost completely covered the wastes. It was also observed that *F. culmorum* did not produce spores on the complement of human wastes. It appears that a complete complement of fungi, SPA and starch phosphoric acid are the proper constituents to begin the processes of the fungal decay of human wastes.

23. EXAMPLE 23

Vault Toilet Applications of *M. albus* and *F. culmorum*

The *M. albus* and *F. culmorum* were grown on barley seed. The seed was then dried and coarsely ground and then placed in at least four vault toilets in the Gallatin National Forest, in the vicinity of Bozeman, Mont. Toilets in a number of locations received 0.75 lb of both of these fungal organisms, along with 1.5 lb of the starch/phosphoric acid mixtures. Untreated control vault toilets were also designated. After one to three weeks there was a noticeable reduction in the odors of associated with each treated toilet as contrasted to the untreated control vaults. There was also a noticeable reduction in the number of flies associated with the treated toilets. After ten weeks it was possible to see fungal growth in the treated toilets. A reduction in the height of the waste mounds in the treated vault toilets was also noted.

In order to determine if any of the volatile antibiotic-like compounds of *M. albus* (6) were associated with the complex biological system present in the vault toilet, a method was used that had been devised previously to analyze the gases in the air space above the *M. albus* mycelium growing in Petri plates (6). First, a "Solid Phase Micro Extraction" syringe was used as a mechanism for trapping the fungal volatiles. This fiber was suspended immediately above (15-25 cm) the waste pile in a treated and in a control vault toilet for 45 minutes. The fiber material (Supelco) was 50/30 divinylbenzene/carburen on polydimethylsiloxane on a stable flex fiber. The syringe was then immediately brought back to the lab and directly inserted into a gas chromatograph (Hewlett Packard 5890 Series II Plus) equipped with a mass-selective detector. A 30 m×0.25 mm I.D. ZB wax capillary column with a film thickness of 0.50 mm was used for separation of the volatiles.

The column was temperature-programmed as follows: 25° C. for two minutes followed to 220° C. at 5° C./min. The carrier gas was Helium Ultra High Purity (local distributor) and the initial column head pressure was 50 kPa. The He pressure was ramped with the temperature ramp of the oven to maintain a constant carrier gas flow velocity during the course of the separation. Prior to trapping the volatiles, the fiber was conditioned at 240° C. for 20 minutes under a flow of helium gas. A 30-second injection time was used to introduce the sample fiber into the gas chromatograph. The gas chromatograph was interfaced to a VG 70E-HF double focusing magnetic mass spectrometer operating at a mass resolution of 1500. The mass spectrometer was scanned at a rate of 0.50 second per mass decade over a mass range of 35-360 amu. Data acquisition and data processing were performed on the VG SIOS/OPUS interface and software package. Initial identification of the unknowns produced by *M. albus* was made through library comparison using the NIST database (6).

Compounds 1-butanol 3-methyl and 2-heptanol 2-methyl were both detected in the vault toilet containing *M. albus* and not in the sample made of the untreated (control) vault toilet. These two compounds are also produced by *M. albus* in culture and have antimicrobial properties.

Additional experiments were performed using citric acid rather than phosphoric acid as the buffer. Like phosphoric acid, citric acid has three carboxyl groups, each of which has a pKa value. The negative log of the acid ionization constant (pKa) is defined as the ability of an ionizable group of an organic compound to donate a proton in an aqueous media. In the case of citric acid, the pKa values for each of its three carboxyl groups are 3.08, 4.39 and 5.49, respectively. Because these pKa values bracket the pH that is most desirable for fungal growth, citric acid is a highly effective buffer in the context of the present invention. By extrapolation, it is believed that any organic compound, natural or synthetic, that has three pKa's will serve the buffering purposes described herein. Dicarboxylic acids (such as malonic, succinic, maleic, glutaric and tartaric acid) may also work in some cases.

Although phosphoric acid was initially used to buffer the human wastes, citric acid was discovered to be more compatible with fungal storage in the WAG BAG®. Specifically, experiments showed that the citric acid does not cause disintegration of the WAG BAG® and is more compatible with both fungi over time. The following experiments were performed with citric acid.

24. EXAMPLE 24

Testing of Citric Acid as Buffer

The following ingredients were added to the WAG BAG® (which included the contents described in connection with Example 1 above): a mixture of *M. albus* and *F. culmorum* fungi at a ratio of 1:1 (by weight); and a mixture of potato starch and citric acid at a ratio of 5:1 (by weight). Approximately equal portions (5 to 6 grams each) of the fungus mixture and starch/citric acid mixtures were placed in each bag. Lastly, 250 to 300 grams of mixed solid and liquid human waste was added to each bag.

Odor was then measured on a scale of 0 (no detectable odor) to 10 (totally repulsive). A panel of at least seven people assessed the odors emanating from the WAG BAGs®. The results are reflected in Table 7 below:

TABLE 7

| | |
|---|---|
| Control WAG BAG ® (with no fungi) at 0 days; odor = | 10 |
| Complete WAG BAG ® (all ingredients) at 0 days; odor = | 10 |
| Control WAG BAG ® (with no fungi) at 30 days; odor = | 10 |
| Complete WAG BAG ® (all ingredients) at 30 days; odor = | 4 |
| Control WAG BAG ® (with no fungi) at 60 days; odor = | 10 |
| Complete WAG BAG ® (all ingredients) at 60 days; odor = | 2 |
| Control WAG BAG ® (with no fungi) at 90 days; odor = | 10 |
| Complete WAG BAG ® (all ingredients) at 90 days; odor = | 0 |
| Control WAG BAG ® (with no fungi) at 120 days; odor = | 10 |
| Complete WAG BAG ® (all ingredients) at 120 days; odor = | 0 |

The results showed that the WAG BAG® ingredients began to reduce the odor of human waste within three to four weeks and totally reduced it to zero after 90 days.

In addition to the odor tests, bacteria were counted according to the techniques previously described. Relative to 0 days, there was a 30%, 80%, 90% and 95% reduction in total bacterial count in the fungal-treated WAG BAGs(® at 30, 60 90 and 120 days, respectively. In the control WAG BAGs®, the reduction over the same time frame was 5%, 10%, 10% and 12%, respectively.

The use of *M. albus* or *F. culmorum* alone in comparable experiments did not result in bacterial or odor reduction. The two organisms together appear to work in a totally compatible manner to reduce odor and bacterial counts in human wastes.

24. EXAMPLE 25

Citric Acid as Buffer/Animal Wastes

Solid fresh pig waste (250 grams) was applied to the base of a ZIPLOC® plastic cup. To it was added 20 grams of the starch/citric acid mixture (5:1) and 5.0 grams of the *M. albus/ F. culmorum* mixture (prepared at 1:1 by weight). The mixture of fungi was applied evenly to the surface of the solid waste. After seven days, the fungi had completely colonized the surface of the solid animal waste, and the odor was reduced to zero (as evaluated by at least seven witnesses). Either fungus alone was not as effective as the mixture of fungi.

Unless defined otherwise, all technical and scientific terms used herein have the same meaning as commonly understood by one of ordinary skill in the art to which this invention belongs. Although the invention has been described in connection with specific embodiments thereof, it is capable of further modifications, and this application is intended to cover any variations, uses, or adaptations of the invention following, in general, the principles of the invention and including such departures from the present disclosure as come within known or customary practice within the art to which the invention pertains, as may be applied to the essential features set forth above, and as fall within the scope of the appended claims.

REFERENCES 1. www.watermatters.org.uk
2. Cilimburg, A., Monz, C., and Kehoe, S., "Wildland recreation and human waste: A review of problems, practices and concerns," *Environmental Management* 25: 587-598 (2000).
3. Strobel, G. A. and Daisy, B., "Bioprospecting for microbial endophytes and their natural products," *Microbiology and Molecular Biology Reviews* 67: 491-502 (2003).
4. Nelson, Paul E., Toussoun, T. A. and Marasas, W. F. O., *Fusarium Species: An Illustrated Manual for Identification* (University Park: Pennsylvania State Univ. Press.) 37-48 (1983).
5. Ausubel, F. M., Brent, R., Kingston, R. E., Moore, D. D., Seidman, J. G., Smith, J. A., and Struhl, K., eds., *Current Protocols in Molecular Biology* (John Wiley & Sons 1994-97).
6. Strobel, G. A., Dirkse, E., Sears, J., and Markworth, C., "Volatile Antimicrobials from a Novel Endophytic Fungus," *Microbiology* 147: 2943-2950 (2001).

We claim:

1. An isolated culture of endophytic *Fusarium culmorum* strain P-2-24:115 deposited as CBS deposit number 114573.

2. A composition comprising the isolated culture of claim 1.

3. A seed comprising the *Fusarium culmorum* culture of claim 1.

4. The seed of claim 3, wherein the seed is a barley seed.

5. The isolated culture of *Fusarium culmorum* of claim 1, wherein the *Fusarium culmorum* is capable of decomposing human waste products.

6. A method of treating human waste products comprising contacting human waste products with an effective amount of the *Fusarium culmorum* culture of claim 1.

7. The method of claim 6, further comprising adding a buffering agent to the combination of human waste products and *Fusarium culmorum*.

8. The method of claim 7, wherein the buffering agent is selected from the group consisting of phosphoric acid, citric acid, malonic acid, succinic acid, maleic acid, glutaric acid, and tartaric acid.

9. The method of claim 6, further comprising adding a starch to the combination of human waste products and *Fusarium culmorum*.

10. The method of claim 9, wherein the starch is selected from the group consisting of potato starch, corn starch, rice starch and cassava starch.

11. A method of treating animal waste products comprising contacting animal waste products with an effective amount of the *Fusarium culmorum* culture of claim 1.

12. The method of claim 11, further comprising adding a buffering agent to the combination of animal waste products and *Fusarium culmorum*.

13. The method of claim 12, wherein the buffering agent is selected from the group consisting of phosphoric acid, citric acid, malonic acid, succinic acid, maleic acid, glutaric acid and tartaric acid.

14. The method of claim 11, further comprising adding a starch to the combination of animal waste products and *Fusarium culmorum*.

15. The method of claim 14, wherein the starch is selected from the group consisting of potato starch, corn starch, rice starch and cassava starch.

* * * * *